(12) United States Patent
Hammes et al.

(10) Patent No.: US 11,752,109 B2
(45) Date of Patent: Sep. 12, 2023

(54) CONTROLLING WATER RELEASE FROM A DIMENSIONALLY STABLE AQUEOUS COMPOSITION

(71) Applicant: LTS Lohmann Therapie-Systeme AG, Andernach (DE)

(72) Inventors: Florian Hammes, Andernach (DE); René Eifler, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 359 days.

(21) Appl. No.: 16/071,156

(22) PCT Filed: Jul. 17, 2017

(86) PCT No.: PCT/EP2017/050866
§ 371 (c)(1),
(2) Date: Jul. 19, 2018

(87) PCT Pub. No.: WO2017/125376
PCT Pub. Date: Jul. 27, 2017

(65) Prior Publication Data
US 2019/0365662 A1    Dec. 5, 2019

(30) Foreign Application Priority Data

Jan. 20, 2016 (EP) .................... 16152059

(51) Int. Cl.
| | | |
|---|---|---|
| *A61K 9/70* | (2006.01) | |
| *A61K 9/00* | (2006.01) | |
| *A61K 31/485* | (2006.01) | |
| *A61P 25/04* | (2006.01) | |

(52) U.S. Cl.
CPC .......... *A61K 9/7061* (2013.01); *A61K 9/0014* (2013.01); *A61K 31/485* (2013.01)

(58) Field of Classification Search
CPC .. A61K 9/7061; A61K 9/0014; A61K 31/485; A61K 9/703; A61P 25/04
See application file for complete search history.

(56) References Cited

U.S. PATENT DOCUMENTS

| | | | |
|---|---|---|---|
| 2011/0022009 A1* | 1/2011 | Maier ..................... | A61P 25/04 604/290 |
| 2011/0182955 A1* | 7/2011 | Roreger ................... | A61K 8/20 424/401 |
| 2011/0225936 A1* | 9/2011 | Ortenzi .................. | B65D 50/06 53/492 |
| 2013/0226108 A1* | 8/2013 | Maier ..................... | A61P 25/36 604/290 |
| 2015/0094259 A1* | 4/2015 | Musabayane ...... | A61K 31/7076 514/6.5 |
| 2015/0267105 A1* | 9/2015 | Kremer .................... | C09K 8/64 507/101 |

FOREIGN PATENT DOCUMENTS

| | | |
|---|---|---|
| DE | 102008016804 A1 | 10/2009 |
| DE | 102009036485 A1 | 2/2011 |
| WO | 2009/121514 A2 | 10/2009 |

OTHER PUBLICATIONS

Mishra et al, Preparation and characterization of amidated pectin based hydrogels for drug delivery system, J Mater Sci: (2008) 19:2275-2280. (Year: 2008).*
Sriamornsak, Chemistry of Pectin and its pharmaceutical uses: A review, ResearchGate, pp. 206-228, Jan. 2003. (Year: 2003).*
International Preliminary Report on Patentability, PCT/EP2017/050866.
Transdermal Controlled Systemic Medications, Y.W. Chien, Drugs and the Pharmaceutical Sciences, vol. 31.
Polymers in Transdermal Drug Delivery Systems, S. Kandavilli et al., Pharmaceutical Technology, May 2002, pp. 62-80.
Transdermale Pflaster; Spektrum der Wissenschaft Oct. 2003, vol. 42. (Internet translation).

\* cited by examiner

*Primary Examiner* — Mina Haghighatian
(74) *Attorney, Agent, or Firm* — ProPat, LLC; Cathy Moore; Vinisha Joshi

(57) ABSTRACT

The invention relates to systems formed from closed liquid-tight packaging and a preferably dimensionally stable aqueous composition which is sealed therein and which, upon activation, releases a liquid phase essentially composed of water in a time-delayed manner. The invention further relates to methods for manufacturing such systems and the use thereof during the production of self-decomposing transdermal therapeutic systems (TTS).

15 Claims, 2 Drawing Sheets

CONTROLLING WATER RELEASE FROM A DIMENSIONALLY STABLE AQUEOUS COMPOSITION

CROSS-REFERENCE TO RELATEID APPLICATIONS

This application is being filed under 35 U.S.C. § 371 as a National Stage Application of pending International Application No. PCT/EP2017/050866 filed Jan. 17, 2017, which claims priority to the following parent application: European Patent Application No. 16152059.8 EP, filed Jan. 20, 2016. Both international Application No. PCT/EP2017/050866 and European Patent Application No. 16152059.8 are hereby incorporated by reference herein in their entirety.

FIELD OF THE INVENTION

The invention relates to systems consisting of a closed, liquid-tight packaging, preferably film packaging, and of a preferably dimensionally stable hydrous composition included therein that on activation releases a liquid phase consisting substantially of water, and to use thereof.

BACKGROUND OF THE INVENTION

Known from WO 2009/121514 A2 are self-destructing transdermal therapeutic systems (TTS) which comprise an active ingredient, a water-soluble agent that renders the active ingredient unusable, such as potassium permanganate, and a mechanical means for perforation. The effect of the mechanical means for perforation is that when the TTS is removed after use, water is able to reach the water-soluble agent that renders the active ingredient unusable, and that then comes into contact with the active ingredient and then destroys it in the presence of water.

In one embodiment of the invention of this WO, the upper, backing layer of the TTS is situated above a sealed pouch with a water reservoir which may also house the mechanical means for perforation. However, the necessary addition of water in the production of such a system is very difficult to realize, owing to the lack of imperviosity of the sealed-edge pouches. Because of condensing water vapor during the sealing procedure, the pouches lack the requisite imperviosity. Water, however, is absolutely necessary in order to activate the self-destructing TTS.

SUMMARY OF ADVANTAGEOUS EMBODIMENTS OF THE INVENTION

It was an object of the present invention to apply water into a pouch and then to provide this pouch with an impervious seal.

It has now been found that the requisite reliable introduction of water into a pouch and the subsequent impervious sealing of the pouch can surprisingly be resolved through the selection of a wafer based on a low-ester/amidated pectin (LE pectin) (A "wafer" refers here to a sheetlike, preferably dimensionally stable composition in film or foil form). Pectins having a degree of esterification (DE°) below 50%, i.e., with less than 50% esterified polygalacturonic acid units, are capable of gelling with calcium ions. The resulting gel strength is determined by amount of pectin, type of pectin, soluble dry-matter content, pH, and the concentration of calcium ions. On further addition of calcium salt, the calcium optimum is exceeded. This leads to a brittle gel (formation of calcium pectinate, the insoluble calcium salt of pectin) with a strong tendency toward synaresis (emergence of water from the gel). Through the use of such a wafer and through addition of a calcium salt, such as calcium chloride, water emerges owing to synaresis from the gel structure of the wafer with a temporal delay, meaning that no water can evaporate during the sealing procedure. Accordingly, the pouch imperviosity can be ensured.

DETAILED DESCRIPTION OF ADVANTAGEOUS EMBODIMENTS OF THE INVENTION

Figure 1A:
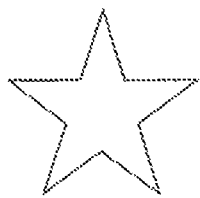
FIG. 1A is an exemplary star-shaped means for undoing the separation between active ingredient and agent.

The invention therefore relates to a system consisting of a closed, liquid-tight packaging, preferably a closed, liquid-tight film packaging, and of a preferably dimensionally stable hydrous composition enclosed therein and optionally comprising a sufficient amount of an activating agent, where the composition releases, with a temporal delay, a liquid phase consisting substantially of water, preferably a system wherein the preferably dimensionally stable hydrous composition is a hydrogel based on a low-ester pectin or on a low-ester amidated pectin, and where the composition comprises as activating agent an alkaline earth or earth metal salt, preferably a calcium salt, more particularly calcium chloride, in an amount sufficient for the temporally delayed release of the liquid phase consisting substantially of water.

These pectin-based compositions preferably contain 2.5-7.5 wt % of pectin, 91-97 wt % of water, and 0.1-3 wt % of a gel-forming alkaline earth or earth metal salt, preferably a calcium salt, more particularly calcium chloride. Particularly preferred are 3.5-6.5 wt % of pectin, 93-96 wt % of water, and 0.2-2 wt % of a gel-forming alkaline earth or earth metal salt, preferably a calcium salt, more particularly calcium chloride. The release of water is induced by addition of preferably a further 0.1-3 wt %, more particularly 0.1-3 wt % of an alkaline earth or earth metal salt, preferably a calcium salt, more particularly calcium chloride.

Low-ester pectins (LE pectins) are pectins having less than 50% esterified polygalacturonic acid units (DE°<50%). They are capable of gelling of calcium ions. In the case of amidated pectins, ammonia is used in place of acid, to replace a proportion of the ester groups by amide groups. This alters the gelling properties in relation to the acidically de-esterified pectins. Like unamidated pectins, LE-amidated pectins require calcium ions for gelling. They form sufficiently firm gels even with small amounts of calcium ions.

It has also been found that hydrogels based on a depolymerized guar gum product as well, such as MEYPROGAT® 90, or on a polyacrylate, preferably sodium polyacrylate, such as ARONVIS® products, are able to release water by synaresis following addition of citric acid. The preferably dimensionally stable hydrous composition of the invention may therefore be a hydrogel based on a depolymerized guar gum product or on a polyacrylate, wherein activation is accomplished by addition of an organic acid, preferably citric acid, in an amount sufficient for the temporally delayed release of the liquid phase consisting substantially of water.

The compositions based on depolymerized guar gum products contain preferably 2.5-7.5 wt % of depolymerized guar gum product and 91-97 wt % of water. Particularly preferred are 3.5-6.5 wt % of depolymerized guar gum product and 93-96 wt % of water. The release of water is induced by addition of 0.1-3 wt %, more particularly 0.1-3 wt % of an organic acid, preferably citric acid.

The compositions based on a polyacrylate, preferably sodium polyacrylate, such as ARONVIS® products, contain preferably 10-34 wt % of polyacrylate and 66-90 wt % of water. Particularly preferred are 16-28 wt % of polyacrylate and 72-84 wt % of water. The release of water is induced by addition of 0.1-3 wt %, more particularly 0.1-3 wt %, of an organic acid, preferably citric acid.

In the case of the compositions where the release of the liquid phase consisting substantially of water takes place following addition of a sufficient amount of an activating agent, the phrase "temporal delay of the release" means that the release sets in after around 0.5-6 min, preferably after around 0.7-4 min, more particularly after around 1-2 min. As a result of this delay, there remains sufficient time for the impervious closing of the packaging, preferably by sealing. The process of release is over after around 1-3 h, preferably after around 1-5 h, more particularly after around 1-10 h.

Furthermore, the preferably dimensionally stable hydrous composition may be a cooled oleic acid/water mixture or a low-melting salt hydrate, preferably calcium chloride hexahydrate, manganese sulfate tetrahydrate, sodium hydrogenphosphate dodecahydrate or lithium nitrate trihydrate. Activation and water release are accomplished here by heating.

The compositions based on a cooled oleic acid/water mixture contain preferably 40-60 wt % of oleic acid and 40-60 wt % of water. Particularly preferred are 45-55 wt % of oleic acid and 45-55 wt % of water. They are produced by preparing at room temperature an emulsion of the components which is then cooled down to 0-1° C., preferably 0-0.5° C., producing a stiff mass which is stored at around 6° C. and can be processed further into wafers. The release of water is induced by warming to around 17-30° C., preferably approximately to room temperature.

The low-melting salt hydrates must be stored and processed below their melting point. Thus calcium chloride hexahydrate melts at around 30° C., manganese sulfate tetrahydrate at around 27° C., sodium hydrogenphosphate dodecahydrate at around 35° C., and lithium nitrate trihydrate at around 28° C., i.e., all below the body temperature (37° C.). The activation and the water release are accomplished here by warming above the melting point, for example approximately to body temperature.

The compositions based on low-melting salt hydrates are suitable for all processes in which warming to approximately body temperature causes release of a liquid phase which consists substantially of water and which is then able to serve, for example, as a solvent for water-soluble substances, or else for activation of water-activatable TTS, or for gas generation, such as the formation of carbon dioxide from mixtures of solid organic acids and inorganic carbonates, for example.

In the case of the compositions wherein the release of the liquid phase consisting substantially of water is induced by heating, the "temporal delay of the release" may be controlled as desired through the temperature of the heat source and the quantity of heat supplied. In the cooled state, the oleic acid/water mixtures, and, below their melting point, the low-melting salt hydrates, can be stored for a relatively long duration without any release of the liquid phase consisting substantially of water.

The closed, liquid-tight packaging in accordance with the present invention is preferably a film packaging, such as a pouch, preferably a sealed flat pouch, more particularly a three-edge or four-edge sealed pouch. The flat pouch comes about through simple folding of the film in the film machine direction. As and when required, the flat pouch may be configured as a three-edge sealed pouch or four-edge sealed pouch. While the three-edge sealed pouch is sealed only at the sides and on the top side, the four-edge sealed pouch receives a sealing seam on the bottom side additionally. By this means, the four-edge sealed pouch, for the same external dimensions, does have a lower volume than the three-edge sealed pouch, but may offer better protection of the pouch against damage.

A precondition for the suitability of plastics for producing liquid-tight film packaging, besides favorable physical properties such as mechanical strength, low inherent weight, and adequate processing properties, is primarily an effective sterilizability, for hygiene reasons. These requirements are adequately met by, for example, polyethylene, polypropylene, polyvinyl chloride, polystyrene, polymethacrylates, polyamides, polyesters, and polycarbonates. These polymers are suitable pouch materials. Preferred are polyethylene (PE, low-density polyethylene and high-density polyethylene) and polypropylene (PP). OPP and BOPP are modifications of PP for altering the properties. A distinction is made here between OPP (PP oriented in one direction) and BOPP (bilaterally oriented PP). These polymers are likewise highly suitable.

The activating agent already added optionally in sufficient amount before closing the packaging of the preferably dimensionally stable preparation, or an increase in temperature, induces the temporally delayed release, after the closing of the packaging, of liquid phase consisting of water and optionally further constituents dissolved therein, from the preferably dimensionally stable hydrous composition.

Additionally included in the pouch, optionally, is at least one mechanical means for opening, perforating or destroying the packaging. This mechanical means may alternatively be affixed on the outside of the pouch, by adhesive bonding, for example. Instead of the mechanical means for opening, perforating or destroying the packaging, or additionally, there may also be another mechanism for opening or destruction integrated into the pouch, such as a weakening point or a predetermined breakage point.

The invention also relates to a method for producing the aforesaid system, this method being characterized in that the preferably dimensionally stable hydrous composition, optionally an activating agent in an amount sufficient for the temporally delayed release of the liquid phase consisting substantially of water, and optionally at least one mechanical means for opening, perforating or destroying the packaging, are introduced into a moisture-tight film packaging and this film packaging is subsequently closed, preferably by moisture-tight sealing.

Another object of the present invention, accordingly, was that of providing a TTS wherein, after use in the manner intended, any abusive removal of the remaining active ingredient remains almost completely impossible, this TTS additionally being readily storable over a relatively long duration and, moreover, ruling out the possibility of transport damage through unintended emergence of agent in solution in liquid.

This further object is achieved through the provision of a TTS, preferably in the form of a transdermal patch for application to the skin surface of the patient, that self-destructs after use, i.e., after removal of the TTS from the skin surface of the patient. Self-destructing TTS means in accordance with the invention that the residual active drug ingredient present in the TTS, after use, is directly or indirectly destroyed, broken down chemically and/or rendered unusable. At the same time, however, it is always ensured that this process of destruction is not started even before or during the transdermal administration of the TTS.

The invention therefore also relates to a self-destructing transdermal therapeutic system (TTS), preferably in the form of a transdermal patch, comprising at least one active ingredient, at least one water-soluble agent that renders the active ingredient unusable, at least one separation between the active ingredient and the agent that renders the active ingredient unusable, and at least one mechanical means for opening, perforating or destroying the packaging, having the effect that when the TTS is removed after use, the separation between the active ingredient and the agent that renders the active ingredient unusable is undone, by ensuring that from an activated system defined above, the liquid phase consisting substantially of water is able to reach the agent that renders the active ingredient unusable and that in this way the active ingredient and the agent that renders the active ingredient unusable come into contact with one another and this contact destroys the active ingredient, i.e., preferably, through chemical reaction, said ingredient is destroyed, is decomposed, or at any rate is rendered unusable.

The agent may be a substance or a substance mixture which may be present in accordance with the invention as a solid or as a paste. The agent is preferably a water-soluble substance which reacts chemically with the active ingredient and thereby destroys it, more particularly a chemical oxidizing agent such as, for example, inorganic reagents such as permanganates, e.g., potassium permanganate, cerium(IV) salts, chromates, nitrites, such as potassium nitrite, peroxo compounds, hypohalides; preferably potassium permanganate and potassium nitrite. With a given active ingredient, the agent is selected preferably on the basis of its chemical reactivity with the active ingredient.

The active ingredient is preferably an active ingredient from the group of analgesics such as, for example, narcotics. Mention may preferably be made of morphine and morphine derivatives, heroin and buprenorphine, or fentanyl and its derivatives remifentanil, sufentanil, and alfentanyl, and also codeine, dihydrocodeine, desomorphine, dextromoramide, dextropropoxyphen, ethylmorphine, hydrocodone, hydromorphone, levomethadone, levorphanol, methadone, metopone, nalbuphine, nicomorphine, oxycodone, naloxone, oxycodone, pentazocine, pethidine, tapentadol, tilidine, or tramadol. Preferred active ingredients are morphine derivatives, heroin, buprenorphine, fentanyl, remifentanil, sufentanil, or alfentanyl. In principle, all opioids which are used as drugs which by a high dependency potential and the life-threatening and destructive unwanted effects, may be rendered unusable after the use by the application of the subject matter of the invention, in order thus to prevent misuse.

In principle it is also possible to use all other combinations of active ingredient and agent for which transdermal administration by a TTS is a suitable form of administration.

Separation between the active ingredient and the agent is normally produced by means of a layer which is permeable to liquids but impermeable to solids, for example a paper, a membrane or a nonwoven web. The web in this context may consist of mineral fibers, such as glass, mineral wool or basalt, animal fibers such as silk or wool, vegetable fibers such as cotton, for example, or manmade fibers made from natural (e.g., cellulose) and/or synthetic polymers. As synthetic plastics it is possible for this purpose to use standard polymers such as, for example, polyamide, polyimide, polytetrafluoroethylene, polyethylene, polypropylene, polyvinyl chloride, polyacrylates or polymethacrylates, polystyrene, polyesters or polycarbonates.

On removal of the patch/TTS from the skin of the patient, the pouch is opened, perforated or destroyed, and the separation between active ingredient and agent is undone, with the ingress of water taking place from the pouch to the agent. The liquid approaches the agent, dissolves it, and so helps the agent to move through, for example, the nonwoven web, come into direct contact with the active ingredient, and destroy it in the process.

The means which accomplishes or enables the ingress of liquid is a mechanical means, which may take a variety of forms. The intention herewith is in any case to ensure that on any removal of the TTS, irrespective of the direction of peeling, the means fulfills its intended function, namely that of allowing, directly or indirectly, the undoing of the separation between active ingredient and agent, an event which, however, must not occur at any earlier time. For this purpose, the means possesses a multiplicity of sharp or pointed regions.

The simplest embodiment of such a means is a star.

A star is shown by way of example in FIG. 1A. Such a star may have sharp points, spikes or edges which, when the flexural radius or the mechanical stress on the TTS reaches a certain point, lead to perforation of at least one adjacent layer, which may be, for example, a wall of a liquid reservoir or a separating film, and which thus accomplish or at least permit the ingress of liquid.

In one preferred embodiment, the mechanical means for perforation possesses a blunt outer contour and a sharp or pointed inlying region.

Figure 1B:
FIG. 1B is an exemplary means having a blunt outer contour and a sharp or pointed inlying region.
Figure 1C:
FIG. 1C is an alternative exemplary means having a blunt outer contour and a sharp or pointed inlying region.

Examples of a geometry of this kind preferred in accordance with the invention are shown in FIG. 1B and FIG. 1C. Both representations show geometries with a round, blunt and hence de-sharpened outer margin, which in accordance with the invention are used with preference. With this geometry, indeed, there is no longer a risk of the opening, perforating or destroying of the packaging taking place prematurely, unintendedly, in the course of production, storage, or transport, or during the intended handling, and therefore of the active ingredient being destroyed even before it is used. The pointed, sharp regions lie protected in the interior of the geometry. At large flexural radii and/or under low force on the TTS, therefore, perforation is not initiated. Only on removal of the TTS from the skin is the flexural radius sufficiently small, or the mechanical forces acting sufficiently large, in order, through distortive bending of the structure, to rotate the corresponding point in the inner region, around pivot points dictated by the geometry, by an angle of up to a maximum of 90°, out of the plane in the direction of the adjacent layer. The tension in the system that is achieved as a result of the stiffness of the material produces perforation of at least one adjacent layer.

It is particularly useful here that the mechanical means that perforates at least one adjacent layer possesses a size which is adapted to the two-dimensional extent of the TTS, and preferably it is only slightly smaller than the internal area of the TTS. On the one hand this ensures sufficient flexibility of the system, while on the other hand the tension in the structure that is achieved by bending is sufficient to perforate the adjacent layer. In addition, a part is also played by the ratio of the length of the point to the total length of the means in force direction. The shorter the length of the point, the more sensitive the system, since shortening the point length increases its stiffness in relation to the overall length of the means. As a result of the action of force such as tension upwardly on removal of the TTS, the point is swiveled about its pivot point/points and then pressed at an acute angle in the range from 20 to 90° through at least one adjacent layer.

Suitable material for the mechanical means is, for example, a flexible plastic of sufficient stiffness. Plastics having such properties are, for example, standard polymers such as polyethylene or polypropylene, polyesters such as polyethylene terephthalate, but also other polymers such as cycloolefin copolymers, polyacrylates or polymethacrylates, polytetrafluoroethylene, PVC, polycarbonate, polystyrene, perfluoroalkoxy polymers (PFA), perfluoroethylene-propylene, etc. The thickness of material influences the effectiveness in the course of use as intended.

The plastics are employed in thicknesses of 100 to 1000 μm, preferably of 200 to 700 μm, more preferably of 250 to 550 μm. As a result of the preferred geometry of the means, namely the ratio of the length of the point to the overall length, and as a result of the arrangement of the pivot points, the TTS is highly flexible and feels pleasant to wear, in spite of the stiffness of the material, without a loss of the self-destruction functionality.

Figure 2:
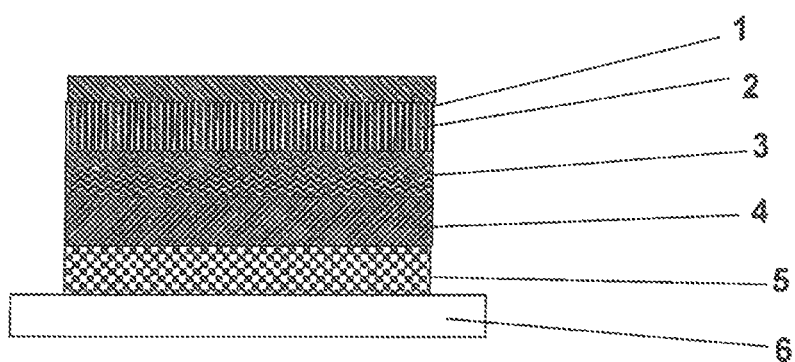
FIG. 2 is a schematic representation of a vertical section through an exemplary inventive TTS.

The self-destructing TTS of the invention possesses in principle a multilayer construction, of which one possible variant is elucidated by way of example in the exemplary embodiment appended as FIG. 2.

FIG. 2 is a schematic representation of a vertical section through a TTS of the invention with one possible multilayer construction. This construction, in the representation, comprises at least one top backing layer 1 which is permeable, for example, to liquids and is made, for example, from woven fabric colored in skin color which on its bottom face is coated at least regionally with a thin layer of adhesive, and a bottom layer 5 of adhesive, which on use of the TTS as intended is in direct skin contact and in which the active ingredient is incorporated. From this layer, the active ingredient is delivered to the uppermost layer of the skin, the epidermis. Not shown in FIG. 2 is the mechanical means for perforation.

Also possible is a membrane patch configuration wherein an adhesive membrane is disposed between an active ingredient reservoir and the skin, and delivers the active ingredient into the epidermis, and is capable of controlling the rate of delivery.

Beneath the upper backing layer 1 is the closed, liquid-tight film packaging 2, containing at least one mechanical means for perforation, this packaging 2 enclosing a preferably dimensionally stable hydrous composition which after activation has releases a liquid phase consisting substantially of water. Beneath the film packaging there is a reservoir 3 for the agent for destroying the active ingredient, preferably an oxidizing agent, such as potassium permanganate in solid form; below that a nonwoven web 4, and below that the layer 5 of adhesive already mentioned above, containing the active ingredient. For storage and transport of the TTS, there is also a transparent protective film 6 beneath the layer 5 of adhesive, and this layer 6 is intended for removal before usage of the TTS.

The TTS of the invention or transdermal patch may otherwise be produced using all of the materials that are known for such systems to the skilled person. For producing the TTS of the invention, therefore, the skilled person is able in principle to employ the materials, production methods, and construction of the TTS or transdermal patches known from the prior art, having additionally—in accordance with the invention—a suitable combination of means and agent (in this regard, cf.: Transdermale Pflaster; Spektrum der Wissenschaft October 2003, 42; Transdermal Controlled Systemic Medications, Y. W. Chien, Drugs and the Pharmaceutical Sciences, vol. 31; Polymers in Transdermal Drug Delivery Systems, S. Kandavilli et al., Pharmaceutical Technology, May 2002, 62-80).

The invention is elucidated in more detail by the examples below, without being confined to them. It is nevertheless possible for specific embodiments of the systems of the invention, described in the examples, individually or in combination with one another, as preferred features for the invention, to be generalized as such. Unless otherwise indicated, % data are % by weight.

Production of Pectin Wafers (See Table 1, Examples 1-4)

Distilled water was stirred in a wide-neck glass in a water bath at about 73° C. with a dispersing stirrer at 200 revolutions per minute (rpm). Pectin classic CU 701 was added slowly in small portions with stirring at 500 rpm. The stirring speed was then raised to 1500 rpm. This produced a pale brown, turbid mass with an increased viscosity. Calcium chloride was weighed out and was added with stirring at a water bath temperature of around 75° C. The speed was subsequently increased to 2000 rpm. After at least 30 minutes, the mass was tested with a glass rod; a gel formed spontaneously. The mass was subsequently applied to the siliconized side of a 100 μm polyester film, which ideally was heated beforehand to a temperature of 50-70 OC. The mass rapidly cured and was able to be lined with a second polyester film by the siliconized side. Wafers could then be produced from this laminate.

Production of a MEYPROGAT® wafer (see table 1, example 5).

Distilled water was stirred in a wide-neck glass with a paddle stirrer at 200 rpm. MEYPROGAT® 90 was added slowly in small portions with stirring at 200-500 rpm. The stirring speed was raised to 2000 rpm. The mass becomes homogeneous and the viscosity rises until the mass can no longer be stirred. Waters could then be produced from the solid mass.

Production of an Oleic Acid Wafer (See Table 1, Example 6).

Oleic acid was introduced in clear form in a wide-neck glass. Distilled water was added and the mixture was homogenized with a dispersing stirrer at 1000 rpm. This produced a milky emulsion. The emulsion was stirred further in an ice bath at around 0.3° C. After approximately 30 minutes, a stiff, white mass was produced. The mass was subsequently stored in a refrigerator at around 6° C. Wafers could then be produced from the stiff mass.

Production of a Sodium Polyacrylate Wafer (See Table 1, Example 7)

ARONVIS® was introduced in a wide-neck glass. Distilled water was added and the mixture was stirred with a glass rod. A solid gel was produced. Wafers could then be produced from the solid mass.

TABLE 1

Production of the dimensionally stable hydrous compositions

| Ex. | Basis | Solvent | Salt for gel | Cation conc. | Salt for water release | Cation conc. for water release | Notes |
|---|---|---|---|---|---|---|---|
| 1 | Pectin Classic CU 701 5% | Water, dist. 94.7% | $CaCl_2$ 0.3% | 0.11% | $CaCl_2$ >0.3% | >0.11% | 1), 2) |
| 2 | Pectin Classic CU 701 5% | Water, dist. 93.5% | Calcium L-lactate 1.5% | 0.28% | $CaCl_2$ >0% | >0% | |
| 3 | Pectin Classic CU 701 5% | Water, dist. 94.1% | Calcium citrate 0.9% | 0.20% | $CaCl_2$ >0% | >0% | |
| 4 | Pectin Classic CU 701 5% | Water, dist. 94.8% | $AlCl_3$ 0.2% | 0.04% | $AlCl_3$ >0.2% | >0.04% | |
| 5 | ®Meyprogat 90 5% | Water, dist. 95% | — | — | Citric acid > 0% | — | 3) |
| 6 | Oleic acid 50% | Water, dist. 50% | — | — | — | — | 4) |
| 7 | Sodium polyacrylate (®Avonis products) 18-26% | Water, dist. 74-82% | — | — | Citric acid > 0% | — | 5) |

Pectin Classic CU 701 is a LE pectin (low-ester pectin).
1) The gels release water when the corresponding salt is added.
2) Water release after addition of $CaCl_2$ between 40-60%, independent of time (valid for cation conc. of 7.8-11.1%, depending on the distribution of the cations in the gel)
3) A non-solid gel is formed; water is released after addition of citric acid.
4) A water/oleic acid emulsion cooled down during stirring, releases water at room temperature
5) A solid gel is formed; water is released after addition of citric acid.

Production of the Synaresis Pectin Wafers of Examples 8-17 from Table 2

These experiments were carried out in PE pouches with zip fastening. For this purpose, squares with a size of around 10 cm² were cut from the pectin wafer laminate (see table 1, examples 1-4). From the wafers now produced, the second polyester film was removed and further calcium chloride was sprinkled on. The sprinkled wafers were subsequently inserted individually into the PE pouches, for further observation, and the zip fasteners were closed.

TABLE 2

Experimental series determining the water loss of a pectin wafer through synaresis, induced by the addition of $CaCl_2$ (pectin used: pectin classic CU 701 5%)

| Ex. | PE pouch tared weight [g] | Gel+ pouch [g] | Gel Specimen 10 cm² [g] | Mass of $CaCl_2$ [g] | Time [h] | Water [g] |
|---|---|---|---|---|---|---|
| 8 | 1.7122 | 2.9812 | 1.2690 | 0.3476 | 2 | 0.5060 |
| 9 | 1.6966 | 2.8983 | 1.2017 | 0.3684 | 22 | 0.5347 |
| 10 | 1.7123 | 2.9218 | 1.2095 | 0.4000 | 46 | 0.6300 |
| 11 | 1.7363 | 2.9724 | 1.2361 | 0.4045 | 70 | 0.5300 |
| 12 | 1.7446 | 2.8032 | 1.0585 | 0.2864 | 144 | 0.6379 |
| 13 | 1.7364 | 3.0426 | 1.3062 | 0.4263 | 168 | 0.6079 |
| 14 | 1.7645 | 3.0407 | 1.2762 | 0.5581 | 192 | 0.7452 |
| 15 | 1.7423 | 3.0303 | 1.2880 | 0.5040 | 216 | 0.7765 |
| 16 | 1.7437 | 2.9705 | 1.2268 | 0.3980 | 240 | 0.5000 |
| 17 | 1.7249 | 2.9757 | 1.2508 | 0.3774 | 312 | 0.3786 |

EXAMPLE 18

Production of a Self-Destructing TTS

Added to 1.14 kg of a solution of a self-crosslinking polyacrylate, consisting of the monomers 2-ethylhexyl acrylate, vinyl acetate, butyl acrylate, and acrylic acid, in a mixture of the organic solvents ethyl acetate, heptane, and isopropanol/toluene, were 100 g of levulinic acid, 150 g of oleyl oleate, 100 g of polyvinylpyrrolidone, 150 g of ethanol, 200 g of ethyl acetate, and 100 g of buprenorphine base. This mixture was stirred over a period of approximately 2 hours until homogeneous. Following homogenization, the mixture was applied to the siliconized side of a 100 m polyester film, after which the solvents were removed by drying in a drying oven at 70° C. for 10 minutes. The coated thickness in the coating was selected such that removal of the solvents produced a weight per unit area of around 80 g/m². Following removal of the solvents, the laminate, consisting of siliconized polyester film and polymer layer containing active ingredient, was lined with a second, less strongly siliconized polyester film. Thereafter the resulting laminate was cut into squares with an edge length of 5×5 cm. The 5×5 cm siliconized polyester film was then removed on one side of the laminate, and an absorbent, liquid-permeable material, a nonwoven web, for example, with a size of 4×4 cm, for example, was adhered centrally. A filter paper pouch with embossed margins, filled with potassium permanganate in powder form, was then placed onto the absorbent, liquid-permeable nonwoven web, the design of the pouch being such that its overall area was smaller than that of the polymer layer containing active ingredient.

Without restriction on the invention, the pouch can have dimensions of 4×4 cm. Then a liquid-tight pouch with all-round sealing and a size of 5 r 5 cm, provided with a four-pointed inverted maltese cross in the manner as shown in FIG. 1C, made from hard polymer material, and with an amount of 1.5 ml of water (released by synaresis from the gel wafer of example 1), was bonded in. When the used TTS is removed from the skin of the patient, at least one point of the maltese cross pierces the lower wall of the liquid pouch and so causes the egress of the water, which enters immediately into contact with the potassium permanganate disposed below it.

When the TTS is administered in the context of its intended use, it is necessary first of all to remove the siliconized polyester layer (protective film), which is easy to accomplish. When the TTS is adhered to the skin of a patient, the water-filled pouch then remains intact to start with. There is no possibility of ingress of liquid to the potassium permanganate powder. When, however, the TTS is removed from the skin of the patient, after the administration period of 1 to 7 days, at least one point of the four-point inverted maltese cross pierces the film of the pouch, owing to the stiffness of the polymer material, and automatically perforates the film. The maltese cross geometry ensures that the pouch is perforated in any case, irrespective of the direction in which the TTS is removed from the patient.

The water is then able to penetrate through the backing film and through the perforation in the separating layer, into the TTS, to dissolve the potassium permanganate, and to transport it through the absorbent nonwoven web to the remaining active ingredient in the bottom layer of adhesive within a short time. An oxidation process is immediately initiated there, and in the case of buprenorphine, for example, results in its oxidative destruction. This ensures that the active ingredient cannot be misused.

The invention claimed is:

1. A system consisting of a closed, liquid-tight packaging, with an optional at least one mechanical means for opening, perforating or destroying the packaging;
    wherein a hydrous composition is enclosed in said liquid-tight packaging, said hydrous composition comprising a sufficient amount of an activating agent, and
    wherein a liquid phase is also enclosed within said closed liquid-tight packaging, and
    wherein said liquid-tight packaging has at least one impervious seal whereby said impervious seal is facilitated by the release of said liquid phase consisting substantially of water that was released from the hydrous composition after a temporal delay;
    the hydrous composition is a hydrogel based on a low-ester pectin or on a low-ester amidated pectin, and where the composition comprises as activating agent an alkaline earth or earth metal salt in an amount sufficient for the release of the liquid phase consisting substantially of water.

2. The system as claimed in claim 1, wherein the closed, liquid-tight packaging is a film packaging.

3. The system as claimed in claim 1, wherein the closed, liquid-tight packaging is a pouch.

4. The system as claimed in claim 1, wherein said system includes at least one mechanical means for opening, perforating or destroying the packaging to facilitate the release of said liquid phase consisting substantially of water.

5. A method for producing a system as claimed in claim 1, wherein the hydrous composition, an activating agent, and optionally at least one mechanical means for opening, perforating or destroying the packaging are placed into a liquid-tight packaging, and the liquid-tight is subsequently closed.

6. The system as claimed in claim 1, wherein the hydrous composition is dimensionally stable.

7. The system as claimed in claim 1, wherein the activating agent is a calcium salt.

8. The system as claimed in claim 1, wherein the activating agent is calcium chloride.

9. The system as claimed in claim 3, wherein the pouch is a sealed flat pouch.

10. A method for producing a system as claimed in claim 5, wherein the liquid-tight packaging is film packaging and the packaging is closed by liquid-tight sealing.

11. The system as claimed in claim 9, wherein said sealed flat pouch is either a three-edge sealed pouch or a four-edge sealed pouch.

12. The system as claimed in claim 1, wherein said temporally delayed release of said liquid phase consisting substantially of water sets in from about 0.5 minute to about 10 hours thereby resulting in an impervious seal in said liquid-tight packaging.

13. The system as claimed in claim 1, wherein the hydrogel is in the form of a wafer—polyester film laminate having two layers.

14. The system as claimed in claim 1, wherein the hydrogel is a brittle gel.

15. The system as claimed in claim 1, wherein said system does not comprise any active drug ingredient.

* * * * *

UNITED STATES PATENT AND TRADEMARK OFFICE
CERTIFICATE OF CORRECTION

PATENT NO. : 11,752,109 B2  
APPLICATION NO. : 16/071156  
DATED : September 12, 2023  
INVENTOR(S) : Hammes et al.

Page 1 of 1

It is certified that error appears in the above-identified patent and that said Letters Patent is hereby corrected as shown below:

On the Title Page

Item [22], PCT Filed:
Delete "Jul. 17, 2017" and insert --Jan. 17. 2017--

Signed and Sealed this  
Twenty-first Day of November, 2023

Katherine Kelly Vidal  
*Director of the United States Patent and Trademark Office*